US008845162B2

(12) United States Patent
Shakespeare et al.

(10) Patent No.: US 8,845,162 B2
(45) Date of Patent: Sep. 30, 2014

(54) COLLIMATED ILLUMINATION USING LIGHT PIPES

(75) Inventors: Tarja T. Shakespeare, Hiltulanlahti (FI); John F. Shakespeare, Hiltulanlahti (FI)

(73) Assignee: Honeywell International Inc., Morristown, NJ (US)

( * ) Notice: Subject to any disclaimer, the term of this patent is extended or adjusted under 35 U.S.C. 154(b) by 617 days.

(21) Appl. No.: 13/101,025

(22) Filed: May 4, 2011

(65) Prior Publication Data

US 2012/0281427 A1    Nov. 8, 2012

(51) Int. Cl.
| | |
|---|---|
| *F21V 7/04* | (2006.01) |
| *G01J 3/02* | (2006.01) |
| *G01J 3/10* | (2006.01) |
| *G01J 3/50* | (2006.01) |
| *F21V 8/00* | (2006.01) |
| *G01N 21/25* | (2006.01) |
| *G01N 21/86* | (2006.01) |
| *G01N 21/57* | (2006.01) |

(52) U.S. Cl.
CPC ........ *G02B 6/001* (2013.01); *G01N 2021/8663* (2013.01); *G01N 21/57* (2013.01); *G01J 3/0205* (2013.01); *G01J 3/10* (2013.01); *G01N 2021/8609* (2013.01); *G01N 21/86* (2013.01); *G01J 3/501* (2013.01); *G01N 21/255* (2013.01)
USPC ............ 362/551; 362/552; 362/555; 362/583

(58) Field of Classification Search
USPC ................................................ 362/551–582
See application file for complete search history.

(56) References Cited

U.S. PATENT DOCUMENTS

| | | | | |
|---|---|---|---|---|
| 6,061,489 | A  * | 5/2000 | Ezra et al. ...................... | 362/551 |
| 7,411,177 | B2 | 8/2008 | Kobayashi | |
| 2007/0052636 | A1* | 3/2007 | Kalt et al. ....................... | 345/83 |
| 2007/0120046 | A1* | 5/2007 | Kobayashi .................... | 250/216 |
| 2008/0180964 | A1* | 7/2008 | Alcelik ......................... | 362/507 |

FOREIGN PATENT DOCUMENTS

| | | |
|---|---|---|
| JP | 10-009813 | 1/1998 |
| JP | 2002-345760 | 12/2002 |
| WO | WO 2007/107849 A1 | 9/2007 |

OTHER PUBLICATIONS

International Search Report dated Nov. 28, 2012 in connection with International Patent Application No. PCT/US2012/034668, 5 pages.
Written Opinion of International Searching Authority dated Nov. 28, 2012 in connection with International Patent Application No. PCT/US2012/034668, 4 pages.
"Light Guide Techniques Using LED Lamps", Agilent Technologies, Dec. 7, 2001, 22 pages.

* cited by examiner

*Primary Examiner* — William Carter (57) ABSTRACT

A system includes multiple light emitting diodes (LEDs) and a light pipe configured to mix light from the LEDs and produce collimated light. The light pipe includes multiple reflective optical devices configured to reflect the collimated light at different angles. The light pipe also includes multiple outlet optical devices configured to selectively control exit of the reflected collimated light from the light pipe. The reflected collimated light has one or more controllable spectral characteristics and/or one or more controllable geometries of illumination.

20 Claims, 7 Drawing Sheets

COLLIMATED ILLUMINATION USING LIGHT PIPES

TECHNICAL FIELD

This disclosure relates generally to illumination systems. More specifically, this disclosure relates to the generation of collimated illumination using light pipes.

BACKGROUND

Webs of material are often used in various industries and in a variety of ways. These materials can include paper, plastic, and other materials formed or processed in sheets. As a particular example, long webs of paper or other material can be manufactured and collected in reels. These webs of material are often manufactured or processed at a high rate of speed, such as speeds of up to one hundred kilometers per hour or more.

It is often necessary or desirable to measure one or more properties of a web of material as the web is being manufactured or processed. For example, it is often desirable to measure the properties of a paper web (such as its basis weight, moisture, color, or caliper/thickness) to verify whether the web is within certain specifications. Adjustments can then be made to the web-making process to ensure the web properties are within the desired range(s).

Many optical- and image-based measurement systems require that a web be illuminated in a specific manner. For example, certain measurements may require that a web be illuminated with light having specific spectral characteristics or at a specific angle. Changes in the spectral characteristics or angle of illumination can prevent proper measurements of the web's properties.

SUMMARY

This disclosure describes the generation of collimated illumination using light pipes.

In a first embodiment, a system includes multiple light emitting diodes (LEDs) and a light pipe configured to mix light from the LEDs and produce collimated light. The light pipe includes multiple reflective optical devices configured to reflect the collimated light at different angles. The light pipe also includes multiple outlet optical devices configured to selectively control exit of the reflected collimated light from the light pipe. The reflected collimated light has one or more controllable spectral characteristics and/or one or more controllable geometries of illumination.

In a second embodiment, an apparatus includes a light pipe configured to mix light from multiple light emitting diodes (LEDs) and produce collimated light. The light pipe includes multiple reflective optical devices configured to reflect the collimated light at different angles. The light pipe also includes multiple outlet optical devices configured to selectively control exit of the reflected collimated light from the light pipe. The light pipe is configured to illuminate a target with the reflected collimated light having one or more controllable geometries of illumination.

In a third embodiment, a method includes transporting light from multiple light emitting diodes (LEDs) through a light pipe. The light pipe mixes the light from the LEDs and produces collimated light for illuminating a target. The method also includes controlling and varying one or more spectral characteristics of the collimated light. The method further includes controlling and varying an angle of illumination of the target, where the light pipe includes multiple reflective optical devices reflecting the collimated light at different angles.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 8, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
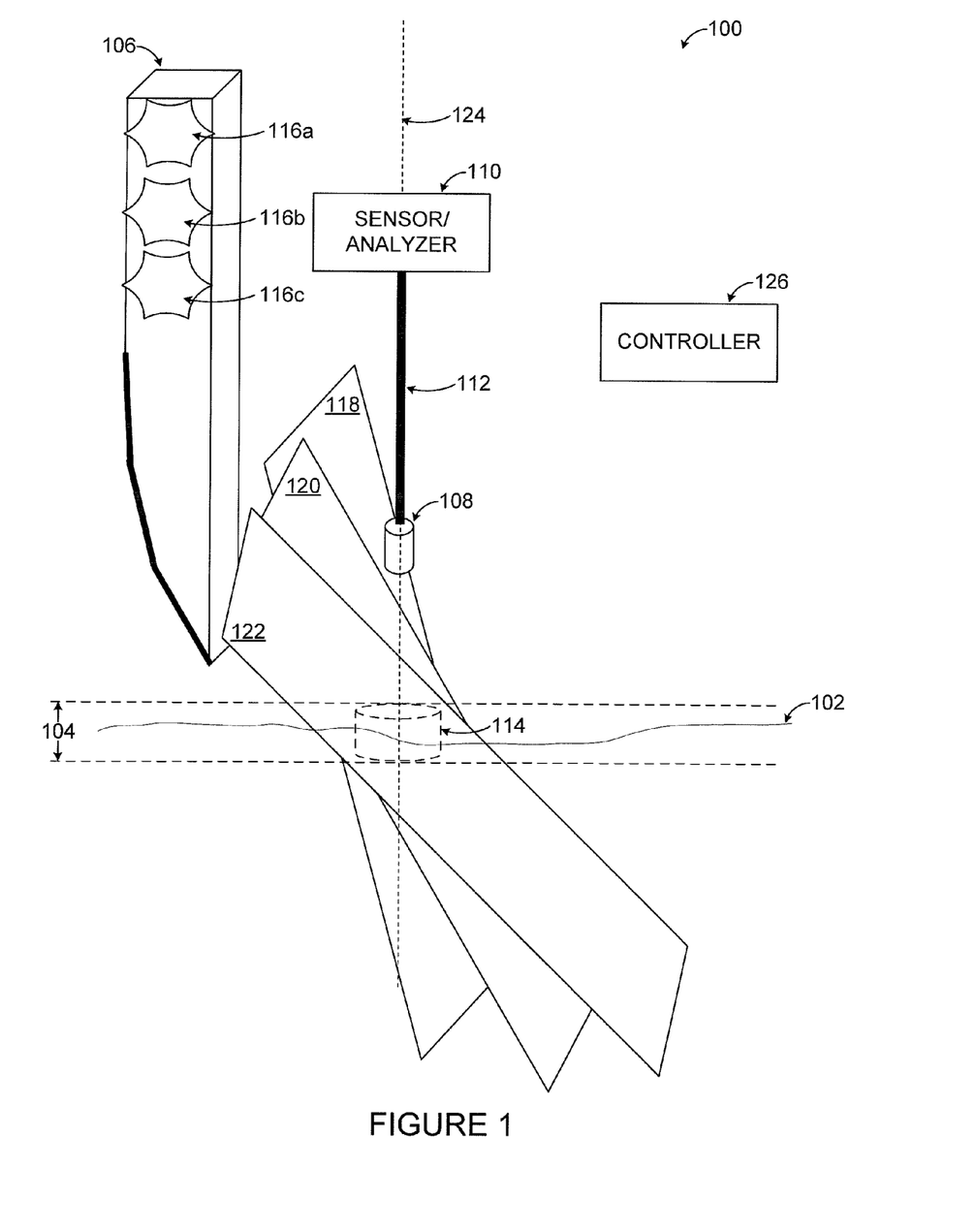
FIG. 1 illustrates an example system using a light pipe to generate collimated illumination according to this disclosure.

FIG. 1 illustrates an example system 100 using a light pipe to generate collimated illumination according to this disclosure. As shown in FIG. 1, the system 100 illuminates and measures one or more properties of a web 102. The web 102 represents any suitable sheet or other web of material being manufactured or processed in some manner. For example, the web 102 could represent a sheet of paper being manufactured by a paper machine and collected at a reel. The web 102 could also represent a paper sheet being processed in some way, such as by placing printing on the paper sheet. The web 102 could represent any other or additional material, such as multi-layer paperboard, cardboard, plastic, textiles, metal foil or sheets, or other or additional materials that are manufactured or processed as moving sheets or other webs.

As shown here, the web 102 may not be stable and can often move within an expected range 104 of positions. This movement can be due to any number of factors, such as air turbulence or other movement created during high-speed manufacturing or processing of the web 102. Depending on the environment, the range 104 of positions could have any suitable dimensions, such as about 10 mm vertically. This means that at any given time, the web 102 could be at any position ±5 mm from a centerline position.

To measure one or more properties of the web 102, the system 100 includes a light pipe 106, collection optics 108, and a sensor/analyzer 110. In general, the light pipe 106 generates light for illuminating the web 102. The light pipe 106 could generate light at any suitable wavelength(s) or in any suitable wavelength band(s), such as light within the visible or ultraviolet spectrum. The light from the light pipe 106 interacts with the web 102, and light that has interacted with the web 102 is received by the collection optics 108. The collection optics 108 could include lenses, filters, or other optical devices to capture light that has interacted with the web 102.

The collection optics 108 provide the captured light to the sensor/analyzer 110, such as through a fiber optic cable or other connection 112. The sensor/analyzer 110 takes measurements of the captured light, such as by measuring spectral or other characteristics of the light that has interacted with the web 102. The sensor/analyzer 110 can then analyze the spectral or other characteristics of the light to determine one or more properties of the web 102. As particular examples, the sensor/analyzer 110 can use the spectral or other measurements of the light to determine the anisotropy, color, gloss, sheen, haze, surface features (such as roughness, topography, or orientation distributions of surface features), or any other or additional properties of the web 102. The determined web properties could then be used in any suitable manner, such as by storing the properties or outputting the properties to a controller that alters a process for manufacturing or processing the web 102.

The collection optics 108 include any suitable structure for capturing light that has interacted with a web and providing the captured light for analysis. The sensor/analyzer 110 includes any suitable structure for measuring and analyzing collected light from a web to determine one or more properties of the web. The sensor/analyzer 110 could, for instance, include a spectrometer for measuring spectral characteristics of the light collected from the web 102. The sensor/analyzer 110 could also include a processing device for analyzing the measurements, such as a microprocessor, microcontroller, digital signal processor, field programmable gate array, or application specific integrated circuit.

In this example, a single light pipe 106 is shown as being used to illuminate a defined area of the web 102 within a space 114. However, it is possible to use multiple light pipes 106 to illuminate the same defined area of the web 102. The defined area of the web 102 may be circular or have any other suitable shape. In some embodiments, the defined area is cylindrical since the web 102 can move up or down within the range 104 of positions. In particular embodiments, light pipes 106 can be distributed angularly around the defined area of the web 102 (with the angular distribution being either uniform or non-uniform) to illuminate the defined area of the web 102 from multiple directions simultaneously. The cylindrical defined area could have any suitable dimensions, such as about 10 mm in height and about 10 mm to about 15 mm in diameter.

As described in more detail below, the light pipe 106 has the ability to control and adjust the spectrum and/or the geometry of light illuminating the web 102. As shown in FIG. 1, the light pipe 106 includes multiple light emitting diodes (LEDs) 116a-116c, which generate light sent through the light pipe 106 to the web 102. Each LED 116a-116c includes any suitable semiconductor structure for generating illumination. The LEDs 116a-116c could, for instance, include LEDs that generate light within the visible or ultraviolet spectrum. Any number of LEDs 116a-116c could be used in the light pipe 106, and light at any number of wavelengths or within any number of wavelength bands could be used. In addition, the light pipe 106 can operate to uniformly mix the spectral irradiance produced by the LEDs 106a-106c and generate a collimated output.

The geometry of light from the light pipe 106 can also be controlled. In this particular embodiment, the light from the light pipe 106 can illuminate a defined area of the web 102 at one of three angles represented by three planes 118-122. The first plane 118 could strike the web 102 at an angle of about 15° to about 20° (as measured from a vertical axis 124). The second plane 120 could strike the web 102 at an angle of about 30° to about 35° (as measured from the vertical axis 124). The third plane 122 could strike the web 102 at an angle of about 45° (as measured from a vertical axis 124). In this way, the light pipe 106 is able to illuminate a defined area of the web 102 at controllable angles, meaning the geometry of illumination is controllable. Note that any number of angles and any angular values could be used here, either individually or in sequential or simultaneous combination.

In this way, the light pipe 106 can be used to precisely control the illumination of the web 102 over a defined area such that the illumination of a portion of the web 102 is not sensitive to the passline of the web 102. The spectral characteristics of light being used to illuminate a defined area of the web 102 can be adjusted by controlling the operation of the LEDs 106a-106c, such as by activating certain LEDs to achieve a desired spectrum of illumination. This allows the appropriate illumination to be created for specific measurements of the web 102. The geometry of the illumination can also be controlled to illuminate a defined area of the web 102 at appropriate angles during specific measurements of the web 102.

In particular embodiments, the light pipe 106 could be placed at least about 5 mm from a centerline position of the web 102 (the centerline being in the middle of the range 104). Also, the light pipe 106 could be placed at a maximum of about 50 mm from the axis 124. In addition, the light pipe 106 could have a maximum height of about 220 mm above the centerline position of the web 102.

Figure 2:
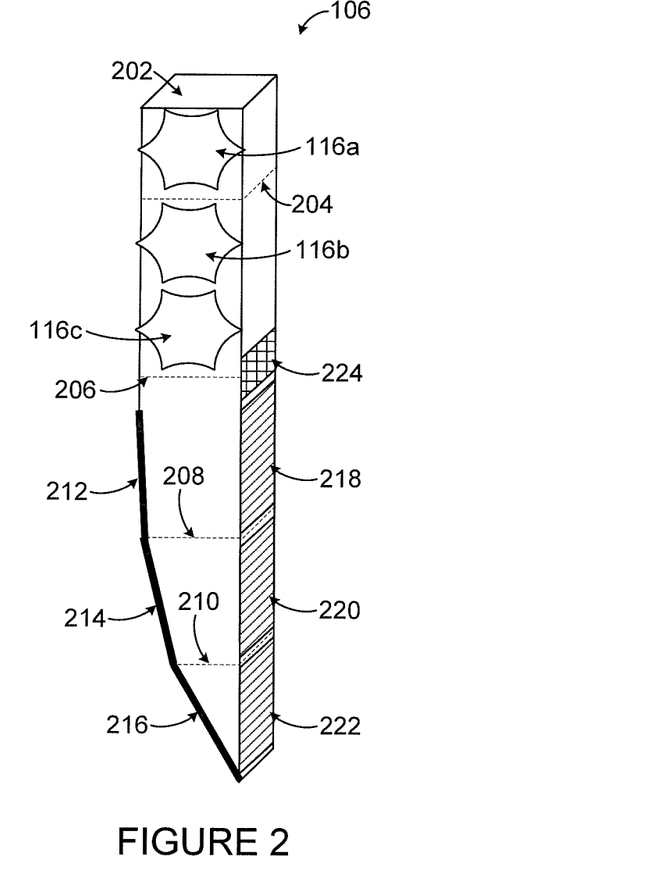
FIG. 2 illustrates an example light pipe for generating collimated illumination according to this disclosure.

The light pipe 106 includes any suitable structure for illuminating a web using a controllable spectrum of illumination and/or a controllable geometry of illumination. Additional details of an example embodiment of the light pipe 106 are shown in FIG. 2.

A perfect collimated light output is distance-insensitive since the light rays are parallel and have no divergence. In reality, it is typically possible to approach perfect collimation, but a collimated output from the light pipe 106 typically has a small non-zero divergence. This is often due to factors such as non-ideal behavior of optical components and economic compromises in the selection of components for the light pipe. However, an approximate collimation using the light pipe 106 with an adequate beam cross-section yields a finite passline insensitivity over some region of the web 102 within the space 114 (the term "passline" denotes the vertical position of an essentially horizontal plane in which the web 102 travels). In other words, if the web's position is perturbed vertically but remains inside the space 114, the intensity of the illumination can stay essentially constant since it is insensitive to the web position within that space 114. In this document, a light output is said to be "collimated" when it is substantially collimated and the intensity of illumination is essentially constant within a specified three-dimensional space 114.

A controller 126 can be used to control the operation of the light pipe 106 in order to control the illumination of the web 102. For example, the controller 126 could control the operation of the LEDs 116a-116c, such as by controlling when the LEDs are flashed. The controller 126 can also control which LEDs are flashed to vary the spectral characteristics of the light from the light pipe 106. The controller 126 includes any suitable structure for controlling the operation of one or more light pipes.

Although FIG. 1 illustrates one example of a system 100 using a light pipe 106 to generate collimated illumination, various changes may be made to FIG. 1. For example, the light pipe 106 could include any number and types of LEDs. Also, the arrangement of the system 100 is for illustration only. Various components in FIG. 1 could be combined, further subdivided, or omitted and additional components could be added according to particular needs. For instance, the collection optics 108 and the sensor/analyzer 110 are shown as being located on the same side of the web 102 as the light pipe 106. However, the collection optics 108 could be located on the opposite side of the web 102 as the light pipe 106. The sensor/analyzer 110 could be placed in any suitable location, whether local to or remote from the light pipe 106 and collection optics 108.

FIG. 2 illustrates an example light pipe 106 for generating collimated illumination according to this disclosure. As shown in FIG. 2, the light pipe 106 includes a housing 202, which supports and protects the other components of the light pipe 106. The housing 202 also typically includes features supporting light transport. This could include reflective inner surfaces that support total or near-total internal reflection of light generated by the LEDs 116a-116c. This could also include reflective paint placed on the outside of the housing 202 to reduce or avoid absorption of external light into the pipe light 106.

The LEDs 116a-116c are shown here as being included within the housing 202. In these embodiments, the LEDs 116a-116c can be optically shaped to forms appropriate for the specific light pipe 106. The LEDs 116a-116c can also be epoxied or otherwise secured within the light pipe 106, although the use of epoxy or similar material is optional. As noted above, any number and types of LEDs could be used in the light pipe 106. Also, the LEDs 116a-116c could be located outside of the housing 202, with light from the LEDs 106a-106c being directed into the housing 202 using suitable optics. In particular embodiments, at least 60% of the flux from each LED is directed through the light pipe 106 to a web.

The light pipe 106 can also include one or more guiding optical devices 204-210 to help guide light from the LEDs 116a-116c through the light pipe 106. A guiding optical device (such as optical device 204) could be used to guide the ray patterns of an individual LED (such as LED 116a). A guiding optical device (such as optical devices 206-210) could also be used to guide the ray patterns of mixed light from multiple LEDs. The guiding of ray patterns could be done to achieve a more optimal shape for light or mixed light within the light pipe 106. Each guiding optical device 204-210 includes any suitable structure for guiding illumination, such as lenses or light guides. The guiding optical devices 204-210 could form part of the light pipe itself (to thereby form a segmented light pipe) or simply be disposed within the light pipe.

The light pipe 106 further includes one or more reflective optical devices 212-216. The reflective optical devices 212-216 reflect light within the light pipe 106 at specific angles. This allows the light pipe 106 to generate illumination for a web at the specific angles. In this embodiment, the light pipe 106 includes three reflective optical devices 212-216 for generating illumination at angles of about 15°-20°, about 30°-35°, and about 45°. However, the light pipe 106 can include any number of reflective optical devices, each associated with any suitable angle. Each reflective optical device 212-216 includes any suitable structure for substantially reflecting or redirecting light. For instance, each reflective optical device 212-216 could include a coatant or a surface mirror placed on a wall or other surface within the light pipe 106. Optics (such as micro-optics or nano-optics) may or may not be used with the reflective optical devices 212-216. The reflective optical devices 212-216 could be formed as integral parts of the light pipe or be installed on surfaces of the light pipe. Different types of reflective optical devices 212-216 could be used.

In addition, the light pipe 106 includes outlet optical devices 218-222. The outlet optical devices 218-222 allow light within the light pipe 106 to exit the light pipe 106 in a controlled manner. For example, the outlet optical devices 218-222 could allow light to exit the light pipe 106 at different angles. Each outlet optical device 218-222 includes any suitable structure for controlling the exit of light from a light pipe. For instance, each outlet optical device 218-222 could include an optical shutter that can be physically opened and closed. Optics (such as micro-optics or nano-optics including diffractive or refractive devices) may or may not be used with the outlet optical devices 218-222. The outlet optical devices 218-222 could be formed as integral parts of the light pipe or installed on a surface of the light pipe. Different types of outlet optical devices 218-222 could be used.

An optional reference outlet optical device 224 could be used with the light pipe 106. In these embodiments, measurements of reference light (light that has not interacted with a web) can be taken and used to determine one or more characteristics of the web. The reference light can be captured through the reference outlet optical device 224. The reference outlet optical device 224 includes any suitable structure for controlling the exit of light from a light pipe.

As shown in FIG. 2, the shape of the light pipe 106 is sloped in a segmented manner at its lower end, meaning the reflective optical devices 212-216 form segments having different slopes. This is for illustration only. The light pipe 106 could have any other suitable shape, such as a tapered, bent, or slanting shape. Also, the controller 126 described above could control the outlet optical devices 218-224 to control when light is allowed to exit the light pipe 106 and at what angle.

In particular embodiments, the light pipe 106 may have the following characteristics. The light pipe 106 can include at least two 10 W LEDs that generate visible light between about 400 nm and about 750 nm in wavelength. The LEDs could include red, green, blue, and white LEDs. The LEDs could also include ultraviolet LEDs, such as NC4U133 LEDs from NICHIA CORPORATION. The light pipe 106 generates collimated light at an angle of about 15° to about 20° in the plane 118, which accounts for about 40% of the total light output from the LEDs. The light pipe 106 also generates collimated light at an angle of about 30° to about 35° in the plane 120, which accounts for about 40% of the total light output from the LEDs. The light pipe 106 further generates collimated light at an angle of about 45° in the plane 122, which accounts for about 20% of the total light output from the LEDs. The LEDs could be flashed (activated intermittently) to generate the needed illumination while reducing thermal management issues. Using flashed LEDs can help to reduce the needed space for the LEDs, as a mounting plate for the LEDs could also be used as a cooling plate. Additional space may be needed if both a mounting plate and a cooling plate are needed for the LEDs.

Although FIG. 2 illustrates one example of a light pipe 106 for generating collimated illumination, various changes may be made to FIG. 2. For example, the light pipe 106 could include any number of LEDs, guiding optical devices, reflective optical devices, outlet optical devices, and reference outlet optical devices in any suitable arrangement.

Figure 3:
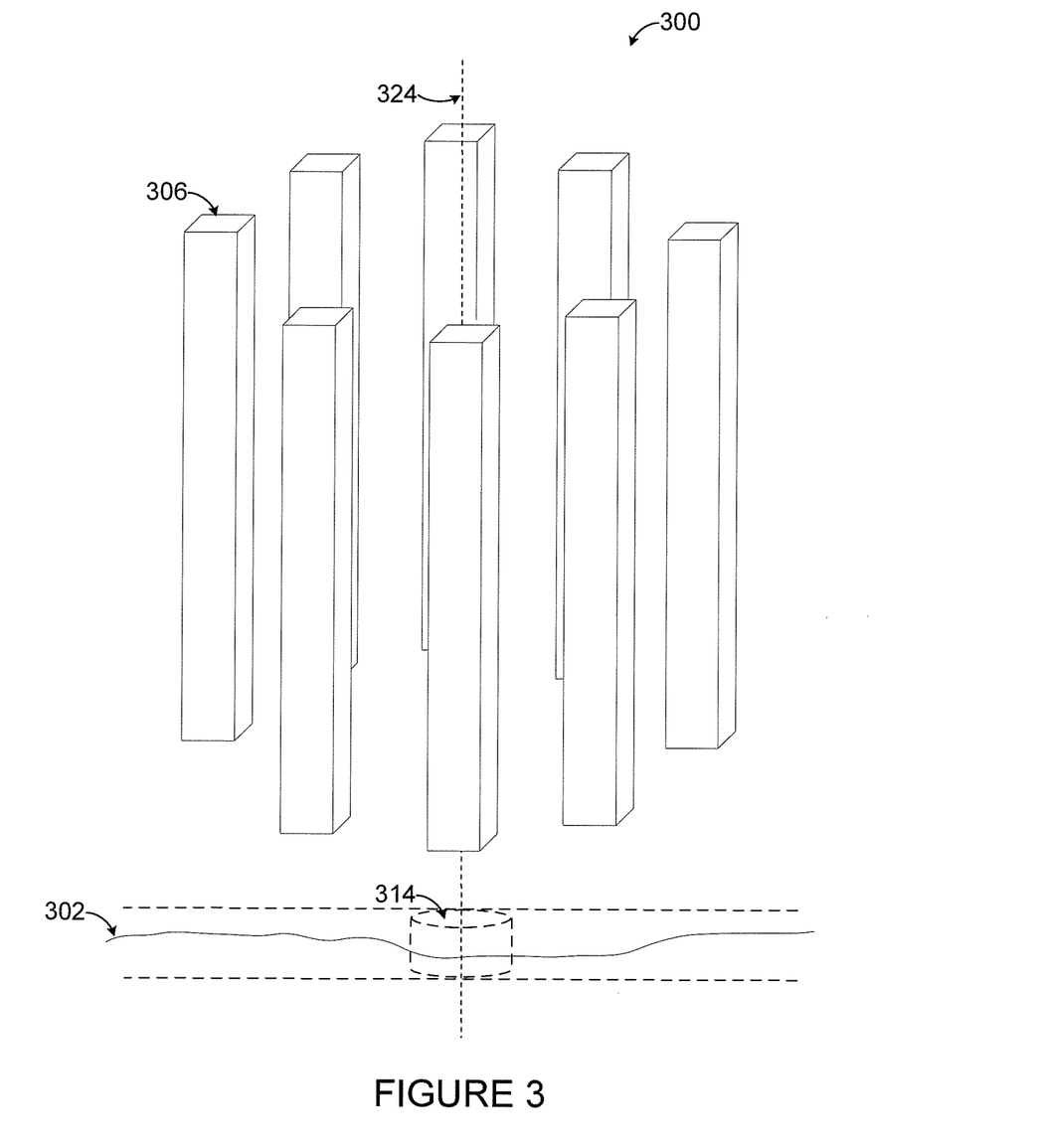
FIGS. 3 and 4 illustrate example systems using multiple light pipes to generate collimated illumination according to this disclosure.
Figure 4:
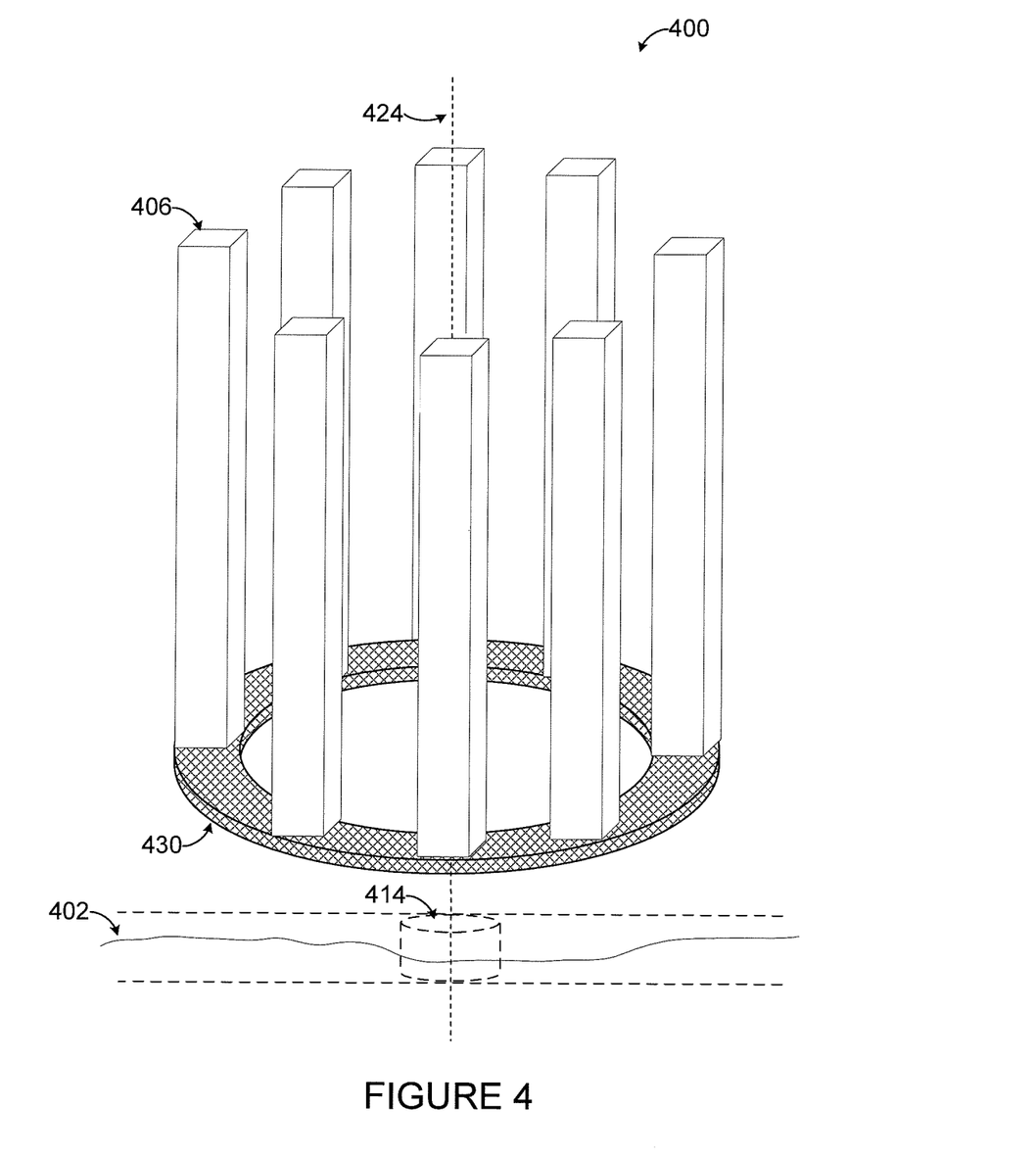

FIGS. 3 and 4 illustrate example systems using multiple light pipes to generate collimated illumination according to this disclosure. As shown in FIG. 3, a system 300 includes multiple light pipes 306 used to illuminate a single defined area of a web 302 within a space 314. The light pipes 306 could be centered around an axis 324. Each of the light pipes 306 could be the same as or similar to the light pipe 106 shown in FIG. 2 and described above.

The number of light pipes 306 used in the system 300 could vary depending on the situation. For example, in some embodiments, the system 300 could include at least four light pipes 306 for illuminating the web 302. Two light pipes 306 could be used to illuminate a defined area of the web 302 in the machine direction, and two light pipes 306 could be used to illuminate a defined area of the web 302 in the cross direction. "Machine direction" refers to the direction along the length of the web 302, which is often the direction in which the web 302 is moving. "Cross direction" refers to the direction across the width of the web 302. The machine and cross direction light pipes 306 can be positioned at an angle of about 90° from one another. In other embodiments, the system 300 could include at least eight light pipes 306.

The use of multiple light pipes 306 allows the web 302 to be illuminated from different directions simultaneously. This supports angular illumination of the web 306 from different directions at the same angle. Each of the light pipes 306 in the system 300 could be operated independently of one another, or groups of light pipes 306 could be controlled collectively. Also, the light pipes 306 need not be identical. For instance, when eight light pipes 306 are used, four light pipes 306 generating visible light can be interleaved with four light pipes 306 generating ultraviolet light. As another example, each light pipe 306 could have its own number and type(s) of LEDs, any drive current for its LEDs, or any suitable angle(s) of illuminating the web 302. In the case that the light pipes 306 are not identical, their spatial arrangement can be chosen to achieve a desired pattern of illumination by each wavelength band of light.

As shown in FIG. 4, a system 400 includes multiple light pipes 406 used to illuminate a defined area of a web 402 within a space 414. The light pipes 406 could be centered around an axis 424. Each of the light pipes 406 could be the same as or similar to the light pipe 106 shown in FIG. 2 and described above.

In this example, the system 400 also includes optics, such as at least one lens 430, to focus light from the light pipes 406 onto the web 402. Any suitable lens 430 could be used here. In this example, the lens 430 is a single torus-shaped or doughnut-shaped lens, such as one formed by bending a rod lens into a circular shape. Any other suitable lenses or other optics could be used here to direct light from multiple light pipes 406 onto the web 402.

Although FIGS. 3 and 4 illustrate examples of systems 300 and 400 using multiple light pipes to generate collimated illumination, various changes may be made to FIGS. 3 and 4. For example, each system 300 and 400 could include any number of light pipes in any suitable uniform or non-uniform arrangement.

Figure 5:
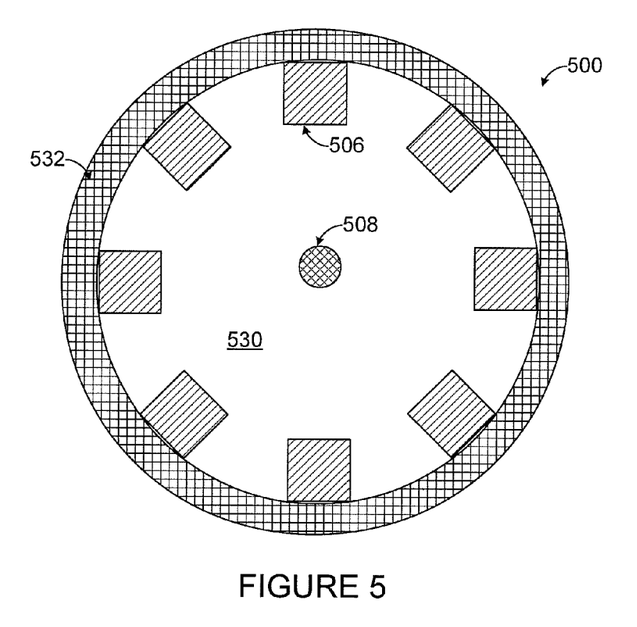
FIGS. 5 and 6 illustrate example support structures for light pipes used to generate collimated illumination according to this disclosure.
Figure 6:
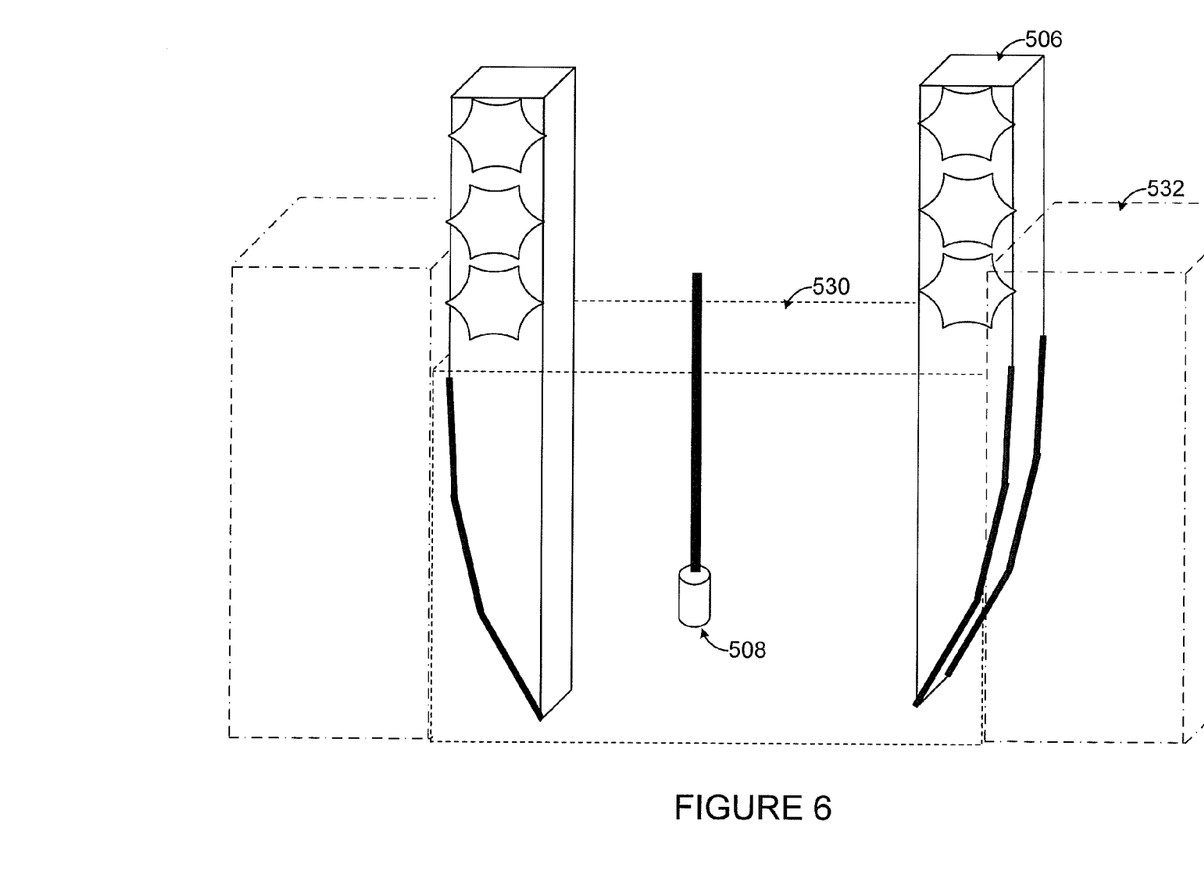

FIGS. 5 and 6 illustrate example support structures for light pipes used to generate collimated illumination according to this disclosure. The light pipes and systems described above may be used in harsh environments. For instance, the light pipes and systems could be used in a dusty environment with a web moving up to about 130 km/hr or more. The temperature of the environment could range from about 10° C. at startup to about 60°-110° C. or more during operation. Common operating temperatures of LEDs could be around 40° C. This can lead to large temperature gradients within the systems.

As shown in FIG. 5, a system 500 includes multiple light pipes 506 and collection optics 508. These components may be the same as or similar to corresponding components described above. In some embodiments, the light pipes 506 include light pipes generating visible light interleaved with light pipes generating ultraviolet light. The system 500 also includes an inner optical block 530 and an outer optical block 532. A cutout of the system 500 across the structure of FIG. 5 is shown in FIG. 6, which illustrates portions of the inner optical block 530 and the outer optical block 532.

The inner optical block 530 can support the light pipes 506, which can be mounted on or within the inner optical block 530. The inner optical block 530 can also support the collection optics 508 to help maintain the optics 508 in a specified position. The inner optical block 530 can further have certain optical features, such as allowing light to pass generally unaltered from the light pipes 506 to a web and from the web to the collection optics 508. In addition, the inner optical block 530 can help to protect the light pipes 506 and the collection optics 508 from dust, oil, water, or other materials that can interfere with the proper operation of a measuring system. The inner optical block 530 could be formed from any suitable material(s) and as any number of parts (which may or may not have common optical features). In other embodiments, the inner optical block 530 could be replaced with an empty space.

The outer optical block 532 can also support the light pipes 506, which can be mounted on or within the outer optical block 532. The outer optical block 532 can further have certain optical features, such as optical surfaces or other optical components formed or mounted on the outer optical block 532. The outer optical block 532 could be formed from any suitable material(s) (such as plastic or aluminum) and as any number of parts (which may or may not have common optical features).

It may be noted that dust or other material may occasionally be deposited on the light pipes or the optical blocks, which can cause backscattering of light or otherwise interfere with proper measurements of a web. In these cases, the sensor/analyzer 110 could use calibrations (such as with a material of known optical characteristics) to at least partially compensate for the interference. Also, the use of the optical blocks 530-532 may facilitate easier cleaning of the system 500 to remove the dust or other material.

In particular embodiments, the system 500 shown in FIG. 5 could have a maximum outer diameter of about 100 mm. Also, if ultraviolet LEDs are used, the inner optical block 530 could be constructed of material that can withstand irradiation by ultraviolet light for a lengthy period of time, such as two years to five years. The system 500 could also be configured to allow easy replacement of the inner optical block 530.

Although FIGS. 5 and 6 illustrate examples of support structures for light pipes used to generate collimated illumination, various changes may be made to FIGS. 5 and 6. For example, the optical blocks 530-532 could have any suitable sizes, shapes, and dimensions.

Figure 7:
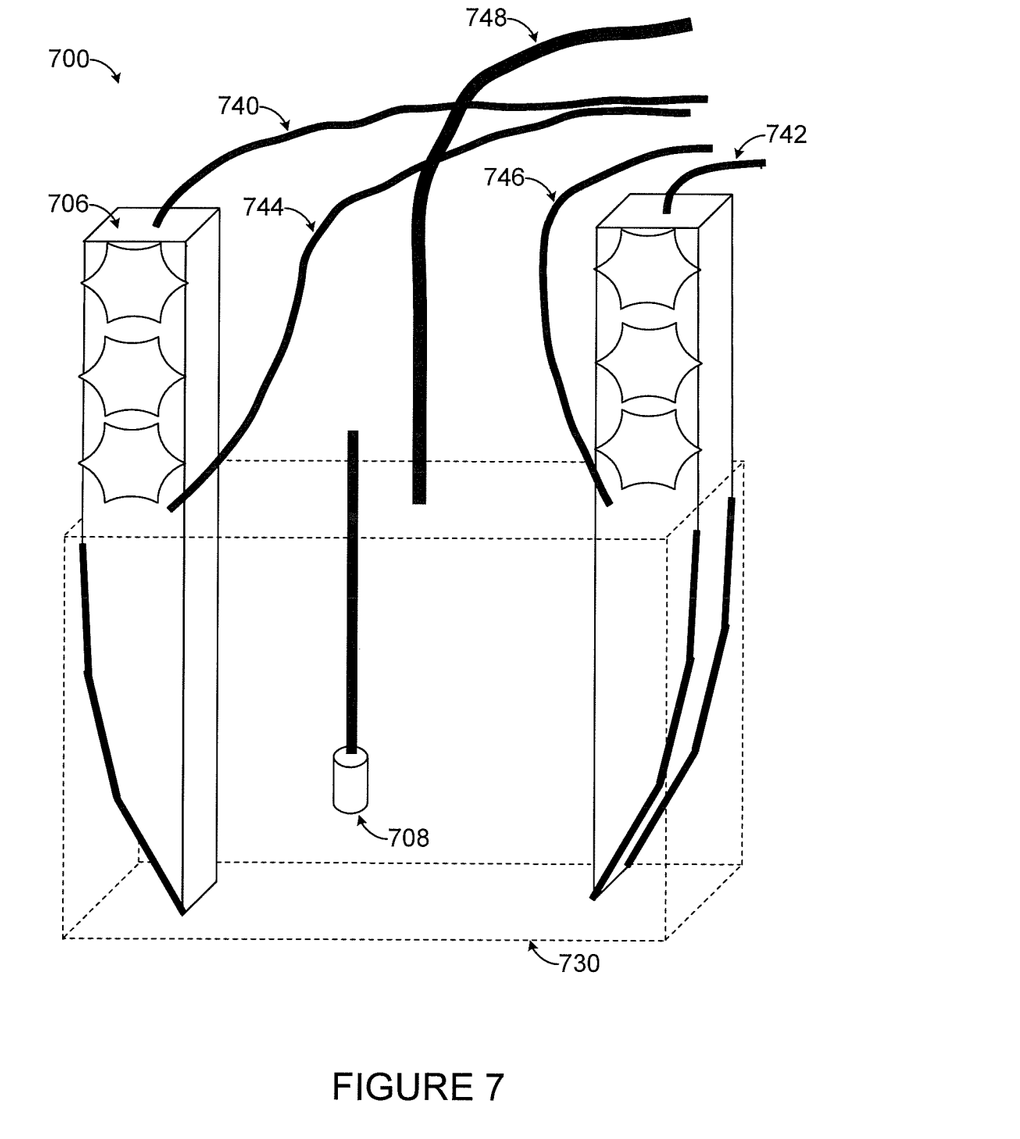
FIG. 7 illustrates an example mechanism for sampling light in a system using light pipes to generate collimated illumination according to this disclosure.

FIG. 7 illustrates an example mechanism for sampling light in a system 700 using light pipes to generate collimated illumination according to this disclosure. In this example, the system 700 includes one or more light pipes 706, collection optics 708, and an inner optical block 730. The system 700 can also include various other components from the systems described above.

As shown in FIG. 7, the system 700 also includes various fiber optic cables or other connections 740-748 used to capture reference light in the system 700. The captured reference light could be provided to any suitable destination, such as a reference spectrometer or other sensor. Measurements of the reference light can be used to determine one or more properties of a web being measured. In this example, the connections 740-742 can capture light at tops of the light pipes 706, and the connections 744-746 can capture light in middle portions of the light pipes 706. However, any number of connections could be used to sample light at any suitable location(s) of a light pipe. The connection 748 samples light at a top of the inner optical block 730. This could be done, for example, to identify any extraneous light interacting with the web. Once again, any number of connections could be used to sample light at any suitable location(s) of the inner optical block 730.

Although FIG. 7 illustrates one example of a mechanism for sampling light in a system 700 using light pipes to generate collimated illumination, various changes may be made to FIG. 7. For example, any other or additional connections could be used to sample any other or additional light in the system 700.

Figure 8:
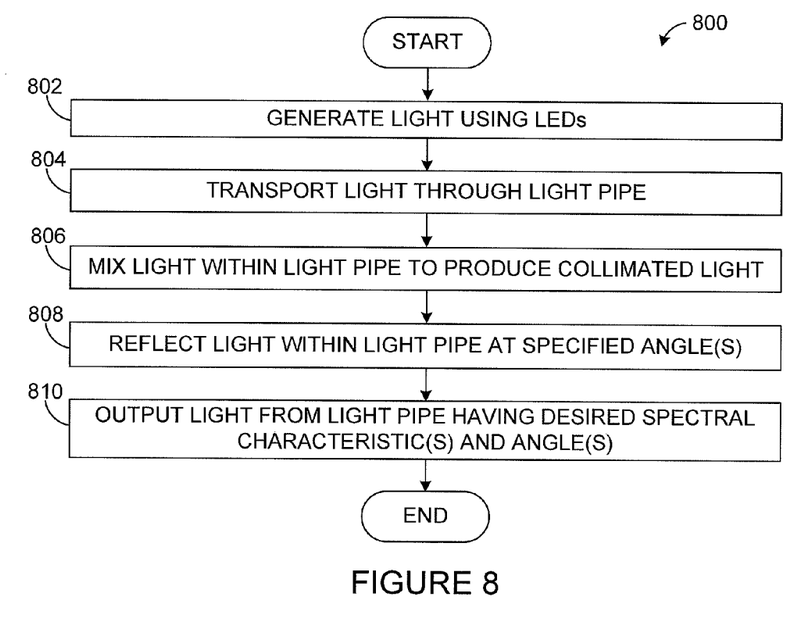
FIG. 8 illustrates an example method for generating collimated illumination using one or more light pipes according to this disclosure.

FIG. 8 illustrates an example method 800 for generating collimated illumination using one or more light pipes according to this disclosure. As shown in FIG. 8, light is generated using multiple LEDs at step 802. This could include, for example, flashing multiple LEDs 116a-116c to generate light at one or more desired wavelengths or wavelength bands. The LEDs can be selected to provide desired spectral characteristics. The light from the LEDs is transported through a light pipe at step 804.

The light is mixed within the light pipe at step 806. This could include, for example, allowing light at different wavelengths or wavelength bands to mix within the light pipe. This could also include collimating the light within the light pipe. The light is reflected within the light pipe at one or more specified angles at step 808. This could include, for example, reflecting the light off one or more reflective optical devices, such as mirrors, within the light pipe.

Light from the light pipe is output at step 810. The light that is output can have one or more desired spectral characteristics, such as light at certain desired wavelengths or within certain desired wavelength bands. The light that is output can also have one or more desired geometries, such as light exiting the light pipe at one or more desired angles.

Although FIG. 8 illustrates one example of a method 800 for generating collimated illumination using one or more light pipes, various changes may be made to FIG. 8. For example, the steps in FIG. 8 can be repeated any number of times within a single light pipe to provide the same output light or different output light. Also, the steps in FIG. 8 can be repeated any number of times within different light pipes to provide the same output light or different output light from the light pipes. In addition, while shown as a series of steps, various steps in FIG. 8 could overlap, occur in parallel, or occur in a different order.

Note that while this document has described the use of at least one light pipe to illuminate a web, the illumination of a web is one example use of the light pipes and systems described above. The light pipes and systems described above could be used to illuminate any other suitable target.

It may be advantageous to set forth definitions of certain words and phrases used throughout this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system comprising:
multiple light emitting diodes (LEDs); and
a light pipe configured to mix light from the LEDs and produce collimated light, the light pipe comprising:
multiple reflective optical devices configured to reflect the collimated light at different angles toward a target; and
multiple outlet optical devices each configured to selectively control exit of the reflected collimated light at one of the different angles from the light pipe toward the target;
wherein the reflected collimated light has at least one of: one or more controllable spectral characteristics and one or more controllable geometries of illumination.

2. The system of claim 1, further comprising a controller configured to at least one of:
adjust the LEDs to control the one or more spectral characteristics of the reflected collimated light; and
adjust the outlet optical devices to control the one or more geometries of illumination.

3. The system of claim 1, wherein the reflective optical devices comprise at least one of: reflective coatings and reflective mirrors.

4. The system of claim 1, wherein the outlet optical devices comprise optical shutters.

5. The system of claim 1, wherein the system comprises:
multiple light pipes; and
at least one optical block configured to support the light pipes.

6. The system of claim 5, wherein the at least one optical block comprises:
an inner optical block configured to protect collection optics, the collection optics configured to receive light that has interacted with the target; and
an outer optical block around the inner optical block and the light pipes.

7. The system of claim 5, wherein different light pipes are configured to generate reflected collimated light having different spectral characteristics.

8. The system of claim 5, further comprising:
at least one optical fiber configured to collect reference light from one or more of: the light pipes and the at least one optical block.

9. The system of claim 1, further comprising:
collection optics configured to receive light that has interacted with the target; and a sensor configured to measure one or more characteristics of the light received by the collection optics.

10. An apparatus comprising:
a light pipe configured to mix light from multiple light emitting diodes (LEDs) and produce collimated light, the light pipe comprising:
multiple reflective optical devices configured to reflect the collimated light at different angles towards a target; and
multiple outlet optical devices each configured to selectively control exit of the reflected collimated light at one of the different angles from the light pipe towards the target;
wherein the light pipe is configured to illuminate the target with the reflected collimated light having one or more controllable geometries of illumination.

11. The apparatus of claim 10, wherein the reflective optical devices comprise at least one of: reflective coatings and reflective mirrors.

12. The apparatus of claim 10, wherein the outlet optical devices comprise optical shutters.

13. The apparatus of claim 10, further comprising:
at least one optical block configured to support the light pipe.

14. The apparatus of claim 10, wherein the light pipe further comprises a reference outlet optical device configured to allow reference light from the light pipe to exit the light pipe.

15. The apparatus of claim 10, wherein the light pipe further comprises at least one guiding optical device configured to guide ray patterns of light from at least one of the LEDs.

16. A method comprising:
transporting light from multiple light emitting diodes (LEDs) through a light pipe, the light pipe mixing the light from the LEDs and producing collimated light for illuminating a target;
controlling and varying one or more spectral characteristics of the collimated light; and
controlling and varying different angles of illumination of the target by controlling operation of multiple outlet optical devices of the light pipe, the light pipe further comprising multiple reflective optical devices reflecting the collimated light at the different angles.

17. The method of claim 16, wherein controlling and varying the one or more spectral characteristics of the collimated light comprises controlling operation of the LEDs, the LEDs configured to produce light at different wavelengths or in different wavelength bands.

18. The method of claim 16, wherein the outlet optical devices are configured to selectively control exit of reflected collimated light from the light pipe.

19. The method of claim 16, further comprising:
illuminating the target using multiple light pipes.

20. The method of claim 19, wherein illuminating the target using multiple light pipes comprises illuminating the target using light having different spectral characteristics from different light pipes.

* * * * *